United States Patent [19]

Freytag Von Loringhoven

[11] Patent Number: 4,708,851

[45] Date of Patent: Nov. 24, 1987

[54] ROOM DEODORIZER OR ODORIZER

[75] Inventor: Andreas E. T. W. Freytag Von Loringhoven, Grasse, France

[73] Assignee: Azur Fragrances France S.A., Grasse, France

[21] Appl. No.: 788,104

[22] Filed: Oct. 16, 1985

Related U.S. Application Data

[63] Continuation of Ser. No. 489,833, Apr. 29, 1983, abandoned.

[30] Foreign Application Priority Data

May 3, 1982 [DE] Fed. Rep. of Germany ... 8212730[U]
Sep. 11, 1982 [DE] Fed. Rep. of Germany ... 8225646[U]

[51] Int. Cl.$^4$ ............................................. A24F 25/00
[52] U.S. Cl. .................................... 422/123; 239/53; 239/56; 239/57; 422/5; 422/125
[58] Field of Search ............... 422/4, 5, 122, 123, 422/306, 120, 124, 125, 126; 239/36, 53, 54, 55, 57, 58, 60

[56] References Cited

U.S. PATENT DOCUMENTS

| | | |
|---|---|---|
| 1,700,574 | 1/1929 | Smith . |
| 1,886,429 | 11/1932 | Saeks . |
| 1,920,599 | 8/1933 | Schuh . |
| 1,989,883 | 2/1935 | Redwine . |
| 2,238,476 | 4/1941 | Monteith . |
| 2,241,167 | 5/1941 | Storck . |
| 2,515,310 | 7/1950 | Messina ............................. 422/125 |
| 2,650,742 | 9/1953 | Overbaugh ....................... 239/60 X |
| 2,681,827 | 6/1954 | Racz . |
| 2,757,278 | 7/1956 | Cloud . |
| 3,031,146 | 4/1962 | Albamonte . |
| 3,565,339 | 2/1971 | Curran ................................ 239/60 |
| 3,823,873 | 7/1974 | Miller et al. ......................... 220/41 |
| 3,888,416 | 6/1975 | Lin ................................... 239/60 X |
| 4,009,384 | 2/1977 | Holland ......................... 422/123 X |
| 4,028,045 | 6/1977 | Reihor ............................... 422/4 X |
| 4,194,690 | 3/1980 | Stever et al. ......................... 239/57 |
| 4,336,907 | 6/1982 | Cummins ............................. 239/57 |
| 4,346,059 | 8/1982 | Spector .............................. 422/125 |
| 4,477,414 | 10/1984 | Muramoto et al. ................. 422/125 |

FOREIGN PATENT DOCUMENTS 0093251 11/1986 European Pat. Off. .
418288 12/1910 France .

OTHER PUBLICATIONS

The American Heritage Dictionary (2nd ed.), Houghton Mifflin Co., p. 231, 1982.

Primary Examiner—Barry S. Richman
Assistant Examiner—William R. John
Attorney, Agent, or Firm—Karl F. Ross; Herbert Dubno

[57] ABSTRACT

A room deodorizer for fragrance dispenser comprises a support at least partially enclosing a fleece-like tampon or wick impregnated with the material to be dispensed and formed on one end with a synthetic resin cap which can be pierced by a pin on the support.

2 Claims, 6 Drawing Figures

ROOM DEODORIZER OR ODORIZER

This is a continuation of co-pending application Ser. No. 489,833 filed on Apr. 29, 1983, now abandoned.

FIELD OF THE INVENTION

My present invention relates to a room deodorizer and, more particularly to a device for releasing a deodorizing substance, scent, fragrance or odor into a room to thereby improve the general odor thereof, to eliminate or mask odors which are disagreeable and, in general to provide a pleasant smell to the surroundings.

BACKGROUND OF THE INVENTION

A variety of room deodorizers capable of releasing a deodorant into the space around the deodorizing device have been commercialized in recent years. Some of these devices include deodorant or fragrance holders which are replaceable in a housing shell to which room air is afforded access through openings or the like and through which the fragrance of the deodorant can be released into the ambient air.

Such devices may be affixed adhesively or chemically to surfaces e.g. in a kitchen or sanitary facility to remove or mask cooking and other household odors, can be stood upon a surface of an article of furniture or the like in a living room, bedroom or dining room to remove or mask other household odors or placed at critical locations such as pet dwelling areas to remove specific odors.

In all cases, the devices are intended to make the environment more satisfying by eliminating unpleasant aromas or superimposing more pleasant odors thereon.

For the most part, conventional room deodorizers have hitherto utilized specially formed multipart perforated synthetic housing resins in which the fragrance carrier was disposed, the latter being a bibulous synthetic resin foam layer or a paper or other plastic material which can be treated with, immersed in or saturated with the fragrance in a liquid form.

The fragrance carrier is generally provided in a mat-like configuration and usually requires special holders or the like. The production of fragrance impregnated synthetic resin mats, the need for holders which frequently must be complex and the complex constructions of earlier room deodorizers has made the cost thereof prohibitive in many cases, has created problems in handling and assembling the devices and has resulted in a general failure to use the prior art units as frequently as they might have been used. In some cases, the deodorizer was not sufficiently decorative to allow it to be exposed to view and in other cases it could not readily be used or did not permit replacement of the fragrance carrier.

OBJECTS OF THE INVENTION

It is the principal object of the present invention to provide a room deodorizer or odorizer which obviates the aforedescribed disadvantages.

Another object of this invention is to provide a lightweight easy to handle and esthetic room deodorizer which can be fabricated simply and at low cost so that it can be utilized with greater versatility and ease than earlier room deodorizers.

Still another object of the invention is to provide a room deodorizer which affords especially effective release of a fragrance into the ambient air and does so while having a pleasant appearance and simplicity of design and construction.

SUMMARY OF THE INVENTION

These objects which will become apparent hereinafter are attained in accordance with the present invention by providing the fragrance carrier in the form of a plug or tampon of a fiber fleece material which forms a bibulous wick for the fragrance. Such tampon-like fragrance-carrier wicks composed of a fiber fleece, are extremely inexpensive, easily fabricated and highly bibulous so that they are particularly effective for use as carriers of a fragrance which can be impregnated into the wick in a liquid state. The tampon or plug form, i.e. generally cylindrical, solid configuration, enables them to be disposed in comparatively small housings. Advantageously the fragrance-carrying wick or plug can be forced over a spike, pin or like support in a base of a housing so that practically all surfaces on the end of the plug penetrated by the spike can be exposed to air within the housing. The plug can be readily replaced as the fragrance release diminishes with time by a new plug which can be available, preimpregnated, in a cellophane, plastic or other odor-tight wrapper.

I have found it to be particularly advantageous to form the housing as an artificial flower, in whose calyx the plug, which can have a base at one end, can be inserted, e.g. via a spike as previously described. The synthetic flower can, of course be made true to nature in the manner of sophisticated artificial flowers currently on the market, e.g. of silk, and the fragrance with which the plug is impregnated can be an aroma associated with the particular blossom or flower. The plug or tampon can also be colored to conform to the natural colors of the flower.

According to another embodiment of the invention, the housing surrounding the fragrance plug can be provided with an artificially symmetrical form and with perforations through which the air is afforded access to the plug. Even in this case, the housing may have a decorative or utilitarian function apart from its use as a holder for the plug.

It has been found to be especially advantageous to form the housing of two relatively rotatable shell members which are coaxial and have perforated wall portions. By appropriate relative rotation of these portions, the perforations can be opened or blocked or masked to control the access of the fragrance from the plug through the perforations to the ambient air. It is advantageous in this embodiment to form the housing as a candle holder, as a lamp or the like since the presence of the tampon or plug will in no way adversely affect the utilitarian purpose.

The housing can have still other decorative or utilitarian forms. For example, it can have an egg shape, it can have the configuration of a spice dispenser, and practically any other upright closed configuration. The housing can also have petal configurations or can be formed with one or more members each providing a petal shape or the like.

When a more utilitarian purpose is desired, it can have an upwardly open cup shape, can receive the plug or tampon impregnated with the fragrance in a central portion protected by a perforated wall, and can form a pencil, pen or other utensil holder.

I have found it to be advantageous in some cases to fabricate the housing of porcelain or a light metal such as aluminum, to suspend the housing among or in the same way as hanging plants are supported and even to provide the plug in the center, for example, of a planter for hanging plants. In all cases, it is desirable to leave the plug suitably colored, if need be, fully exposed so that it can be removed and replaced with ease, or to provide it within a structure which affords access to the plug for its replacement.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
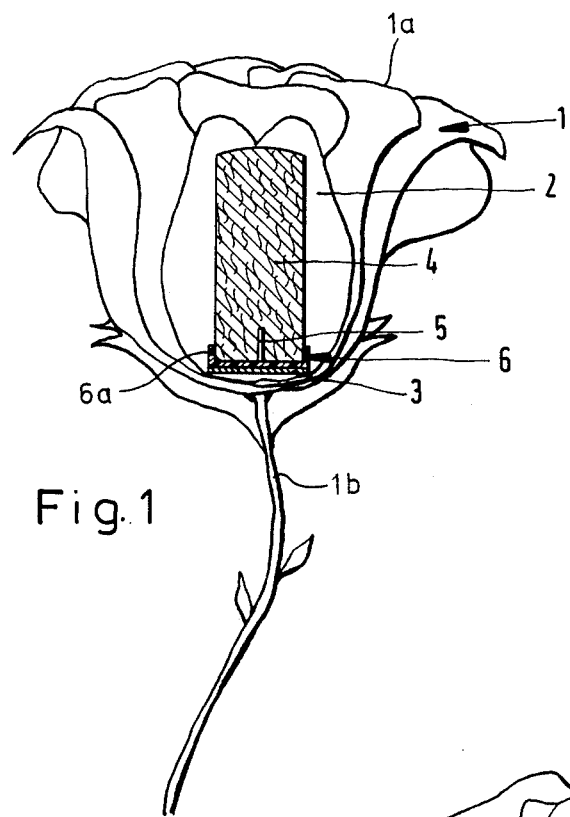
FIG. 1 is an axial cross sectional view through a synthetic flower forming the housing for a plug-like fragrance carrier of a deodorizer according to the invention.
Figure 2:
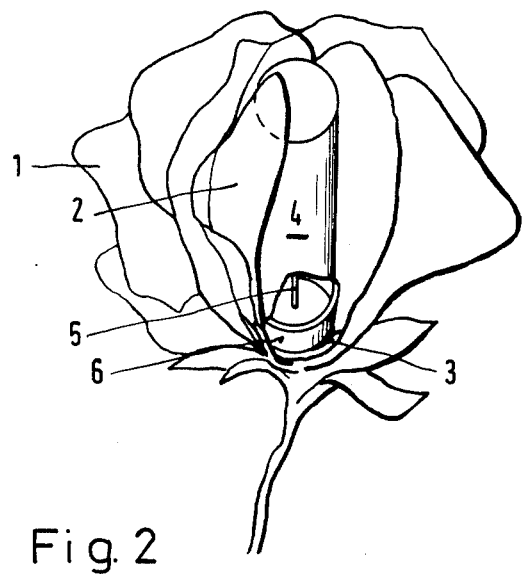
FIG. 2 is a perspective view showing another plug-holder as a room deodorizer according to the invention in a blossom or flower configuration.

FIGS. 1 and 2 show an artificial flower 1, in the illustrated embodiment, a rose, having petals 1a which can be fabricated from synthetic resin or any other material, commonly used in the fabrication of artificial flowers, e.g. silk, on a stem 1b. At the calyx 2 of the flower, completely surrounded by the petals, a small round disk, 3, is fixed in place and forms a seat for a fragrance carrier 4. The latter is a tampon of wicking material, e.g. a synthetic resin or natural fiber which is impregnated with the fragrance so that the latter is released into the atmosphere over a period of time. The tampon is of generally cylindrical configuration and may also be impregnated with other deodorizing substances or materials commonly used in air fresheners and even slow release insecticidal substances or antisepticizing substances.

The tampon or plug 4 is forced onto a pin 5 which is fixed to the disk 3 and which thus retains the plug 4 in place but enables the plug to be removed and replaced.

In order to be certain that the plug 4 will have sufficient absorptive capacity for the fragrance, it may be made exceptionally bibulous and soft, in which case it is possible that it might slip from the pin 5. It has therefore been found to be advantageous to provide the disk 3 with a housing or cup 6 composed of synthetic resin, mounted on the pin 5 for carrying the latter and having an upstanding flange 6a which snugly receives the lower end of the plug 4.

The cup 6 can be bonded, e.g. by an adhesive, to the plug so that it is pierced by the pin 5 of disk 3 when the plug is forced onto the latter and is replaced with the plug when the plug is withdrawn. Alternatively, a cup can be mounted on the disk 3 or the disk 3 can be formed as the cup directly.

The dimensions of the plug 4 will, of course, depend upon the type of flower and the space available for it. In general it will have a length of 1 to 4 cm, a diameter up to 1.5 cm, and will be colored to suit the coloration of the flower. With these dimensions, utilizing a cotton plug, i.e. a plug made from cotton fibers, in room temperature the deodorizing flower can be effective from 4 to 6 weeks before the plug must be changed.

FIGS. 3-6 show other configurations of a room deodorizer utilizing the principles of the present invention. Naturally, these configurations can also be used for room odorizers or for the long term release of insecticides or other vapors into the air. In each case, the fragrance or vapors are released from a fleece in the form of a tampon or plug-like wick 14 impregnated with the material to be released, with or without a suitable carrier, in a liquid form. The highly bibulous plug is capable of absorbing a large quantity of the fragrance and of releasing this fragrance over a correspondingly long period of time or relatively rapidly depending on the access of air to the plug.

In each case, one end of the plug 14 can be fitted into a flat cup-shaped member of the holder, but preferably is provided in advance with the cup-shaped member 16 which can have an adhesive face provided with a pressure sensitive adhesive enabling it to be held in and withdrawn from the holder with the plug. Preferably, however, the holder in each case is provided with a base, e.g. at 13, which can be formed with a pin 15 adapted to pierce cap 16 and the wick easily and thus enable the plug to be mounted or dismounted.

In each case moreover, the device is provided with a housing 11 which can be rotationally symmetrical about the axis of the plug and surrounds the latter while affording access of air thereto or permitting the fragrance to radiate from the plug. In all of these embodiments, moreover, the plug 14 lies along the axis of rotational symmetry of the housing or the device.

Figure 3:
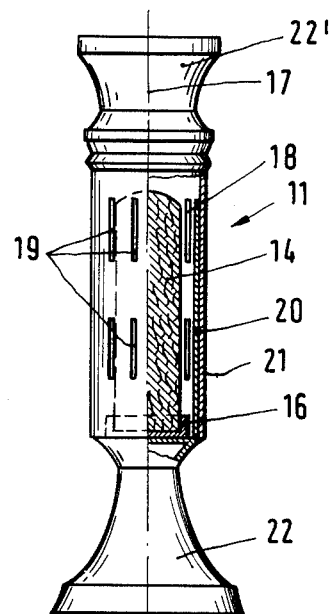
FIG. 3 is a partially axial section and partial elevational view through a candle holder according to the invention.
Figure 4:
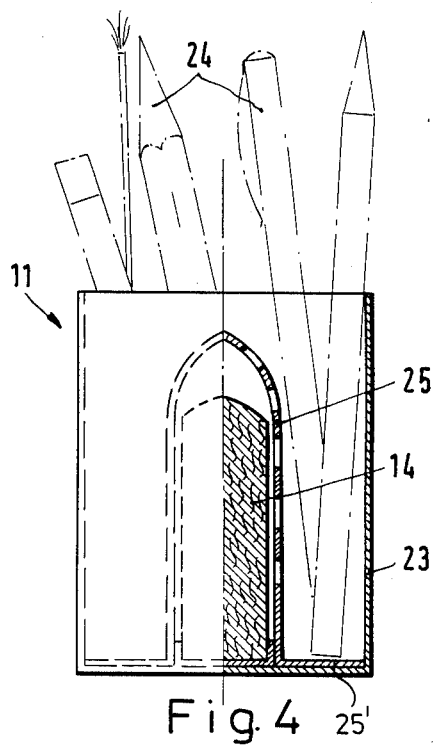
FIG. 4 is a view similar to FIG. 3 showing the application of the invention to a utensil holder, i.e. a desk-type holder for writing instruments.

FIG. 3 shows a housing 11 which is provided with an upper portion 22' which can form a candle or electric lamp socket along the axis 17 upon which the plug 14 is centered. The housing 11 is here composed of two cylindrical housing sleeves 20 and 21 which are formed with respective slits 18 and 19 adapted to be partially or wholly aligned or even disaligned by rotation of the outer sleeve connected to the socket 22' relative to the inner sleeve 20 connected to the base 22. The release of the fragrance can, by relative rotation of the sleeves, be controlled from zero to full release and hence the odorizing or deodorizing effect can be regulated between a negligible value and full deodorant or odorizing effect. In the embodiment of FIG. 4, the housing 11 comprises an outer cup 23 which can form a pencil or like holder, the desk utensils being illustrated at 24 in dot-dash lines. An insert 25, which can be perforated, fits over the plug 14 and has a flange 25' resting on the bottom of the cup 23.

Figure 5:
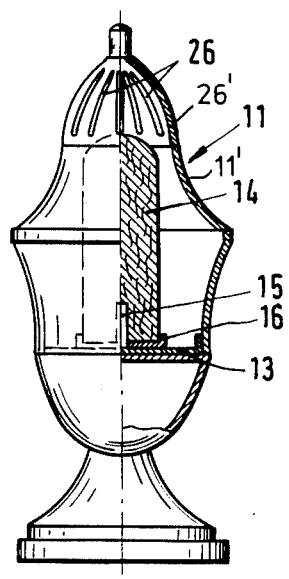
FIG. 5 is a similar view showing a spice container configuration of the housing.

In FIG. 5, the device has the configuration of a spice dispenser and hence the housing 11 has a generally egg shape. The device can be fabricated from tin, pewter or some other esthetically pleasing metal or even from porcelain or glass, generally is opaque, and at the upper end can be provided with the usual slits 26 which, in a functional spice dispenser, can be utilized to dispense the contents. In the embodiment shown, however, these slits, formed on a removable cap 26', serve to allow escape of the fragrance into the environment.

The cap 26' can be threaded onto the body 11' of the housing or connected thereto by a bayonet joint hinge or the like so that it can be removed or swung away to afford access to the plug 14. The base 13 is here provided with the pin 15 over which the cap 16 of the plug 14 is forced.

Figure 6:
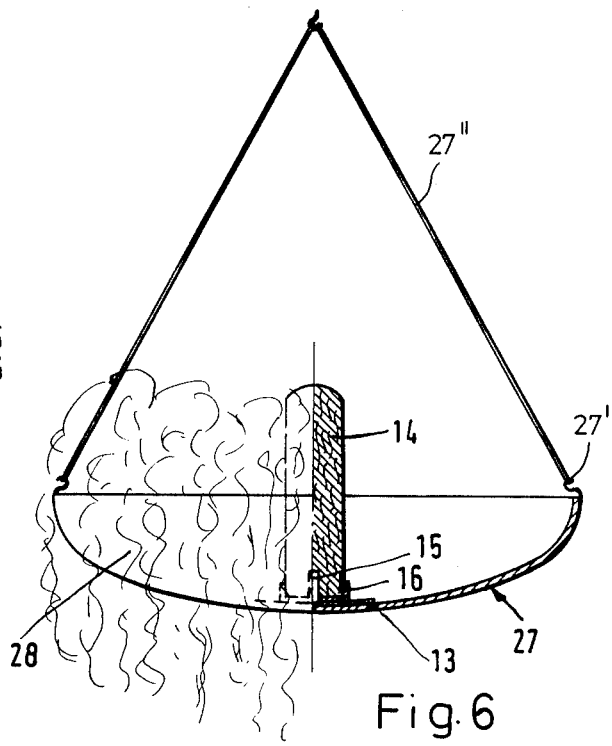
FIG. 6 is another partly sectional and partly elevational view of a hanging planter according to the invention.

FIG. 6 shows a hanging planter utilizing the principles of the present invention. The planter is provided with an upwardly open shell 27 having angularly equispaced hooks 27' for the suspending wires or filaments 27".

At the center of the shell 27, a base 13 is provided to which the metal pin 15 may be welded or soldered, the base 13 being adhesively or otherwise secured to the shell. The plug 15 and the cap 16 may be thrust over the pin 15 and the plug can then be surrounded by a planting 28 which can hang from the shell and prevent the plug from being seen. When the planting has blossoms or flowers, the fragrance emitted by the plug 14 can correspond to the fragrance of these flowers and of course the plug can be colored to correspond to the coloration of the plant.

I claim:

1. A vapor releasing kit for releasing a vapor of a material into a room comprising:
   a synthetic flower having:
      a stem, and
      an upwardly open petal structure defining an interior space open to the atmosphere and delimited from below by a base and laterally by an array of petals extending upwardly around said space from said base, said stem being attached to the exterior of said base and extending downwardly therefrom;
   a rigid member fixed to said flower at said base and positioned within said interior space;
   a single solid rigid pin upstanding from said member and extending into said space; and
   a tampon disposed in said space and impregnated with a material in vaporizable liquid form engaged by said pin, said tampon comprising:
      an elongated plug of a flexible, fibrous, bibulous material impregnated with said liquid,
      a cap of synthetic resin material bonded to said plug at a lower end thereof and having a rim enclosing said lower end of said plug, said cap enabling said plug to be retained on the pin and being transfixed and pierced by said pin, said pin extending into said plug through said cap to removably retain said tampon on said member, and a disposable wrapping impermeable to vapors of said liquid and surrounding said tampon and capable of being removed prior to said tampon being disposed within said space.

2. A vapor releasing kit according to claim 1 wherein said bibulous material is a fleece material.

* * * * *